(12) United States Patent
Fedegari

(10) Patent No.: US 8,163,234 B2
(45) Date of Patent: Apr. 24, 2012

(54) METHOD FOR CHARACTERIZING BIOLOGICAL INDICATORS IN STERILIZATION PROCESSES AND APPARATUS FOR THE IMPLEMENTATION THEREOF

(75) Inventor: Fortunato Fedegari, Pavia (IT)

(73) Assignee: Fedegari Autoclavi SpA, Albuzzano (Pavia) (IT)

( * ) Notice: Subject to any disclaimer, the term of this patent is extended or adjusted under 35 U.S.C. 154(b) by 1564 days.

(21) Appl. No.: 11/387,272

(22) Filed: Mar. 23, 2006

(65) Prior Publication Data
US 2006/0216825 A1     Sep. 28, 2006

(30) Foreign Application Priority Data
Mar. 24, 2005   (IT) ............................... MI2005A0506

(51) Int. Cl.
*G01N 31/22*     (2006.01)
(52) U.S. Cl. ............... 422/3; 422/68.1; 422/430; 436/1; 435/31; 435/287.4
(58) Field of Classification Search ............. 422/3, 68.1, 422/430; 436/1; 435/31, 287.4
See application file for complete search history.

(56) References Cited

U.S. PATENT DOCUMENTS
2002/0160440 A1* 10/2002 McDonnell et al. ............ 435/31
2004/0062692 A1* 4/2004 Lin et al. ....................... 422/297

FOREIGN PATENT DOCUMENTS
EP    1 052 507 A    11/2000
EP    1 493 449 A    1/2005

* cited by examiner

*Primary Examiner* — Lyle Alexander
(74) *Attorney, Agent, or Firm* — Fredrikson & Byron, P.A.

(57) ABSTRACT

The invention relates to a method for characterizing the bioindicators in sterilization processes using an autoclave and the like, in which a bioindicator is kept in the same conditions as the sterilization chamber (2) and extracted after a predetermined time interval. For this purpose the chamber (2) has, passing through it, a tube (5) on the ends of which valves (8-9, 10-11) are mounted, said valves allowing the insertion, from above, of a bioindicator sample and its extraction from below, when required, without a significant loss of sterilizing agent. Alternatively, the duct (5) may also be arranged outside the sterilization chamber (2) and kept in communication therewith by a bypass connection.

20 Claims, 5 Drawing Sheets

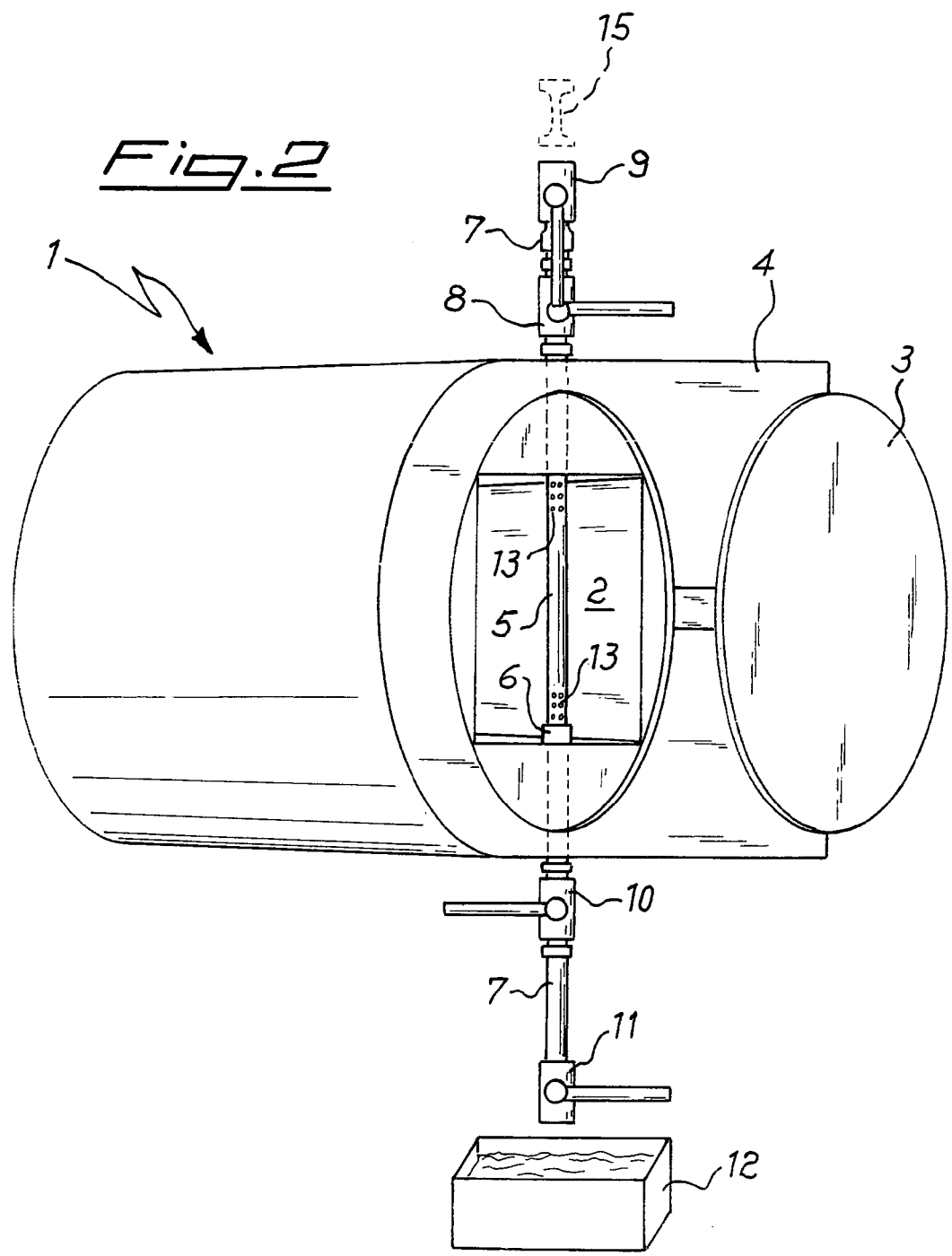

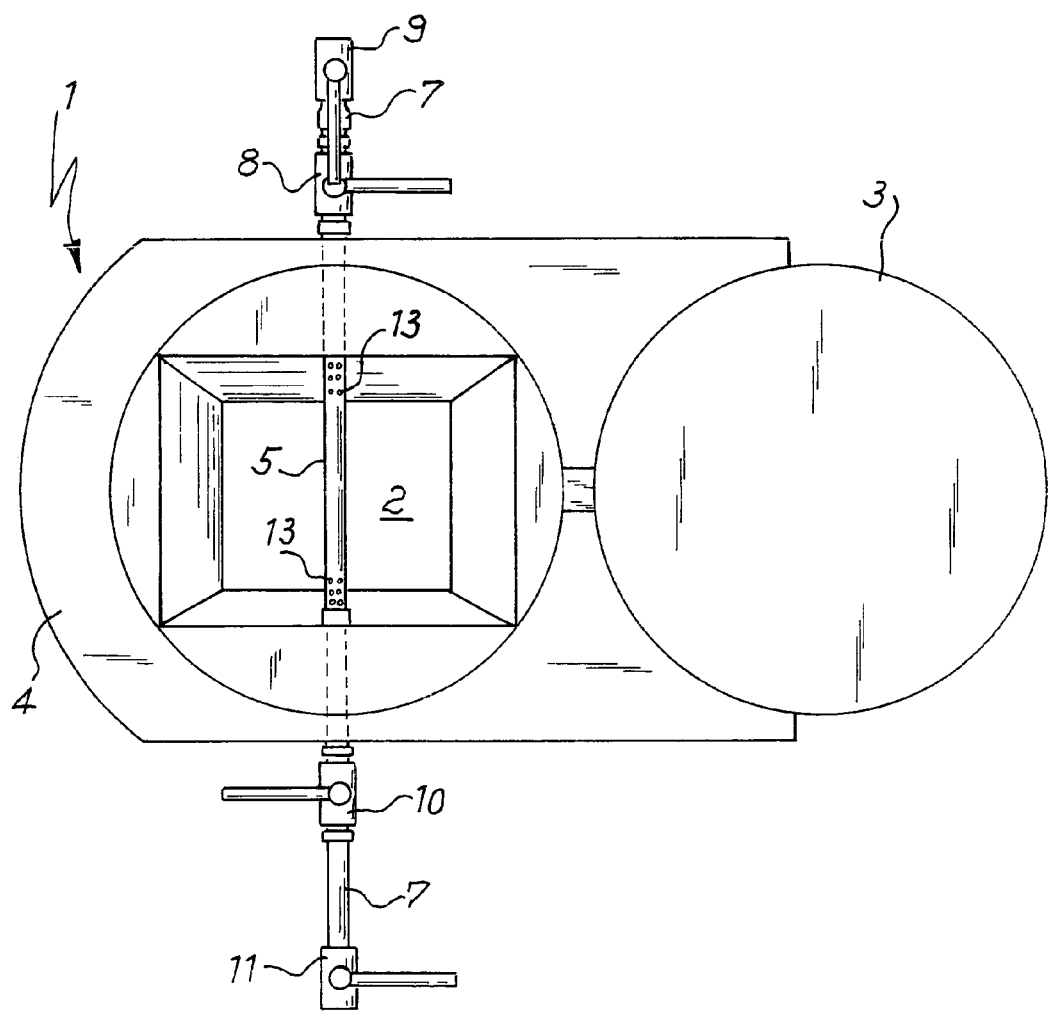

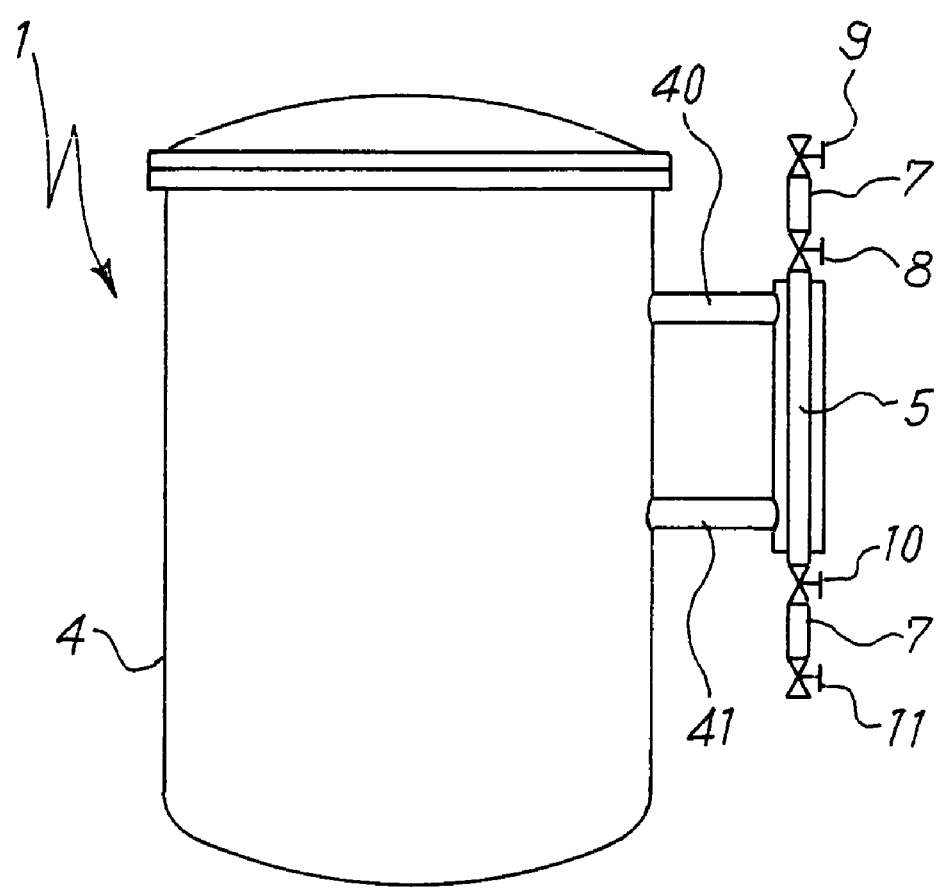

METHOD FOR CHARACTERIZING BIOLOGICAL INDICATORS IN STERILIZATION PROCESSES AND APPARATUS FOR THE IMPLEMENTATION THEREOF

RELATED APPLICATIONS

This application claims priority to Italian Patent Application No. MI2005A000506 filed Mar. 24, 2005, the teachings of which are incorporated herein by reference.

BACKGROUND OF THE INVENTION

The invention relates in general to the monitoring of sterilization processes in the pharmaceutical, food, sanitary and similar fields.

SUMMARY OF THE INVENTION

As is known, an important aspect of the sterilization processes is monitoring of the total destruction or the degree of reduction in the microbic content of the product undergoing treatment.

Typically, said monitoring is performed using two methods which are employed alternately and are also applicable in parallel.

The first method is of the physical type (measurement of physical parameters such as temperature, pressure, concentration of the sterilizing agent) and in the case of wet heat processes (such as, for example, saturated steam processes) aims to ensure that the coldest point in the charge has also reached the minimum sterilization temperature. The abovementioned values are those considered by the operator suitable for the complete destruction of the microbic content potentially present in the product. The detection of the minimum physical sterilization parameters by the sensors may, in some cases, not be sufficient to ensure the actual sterilization of the product; in fact both the position of the sensors, and the type of physical parameter detected, always provide indirect or incomplete information as to the overall performance of the process.

In the case of steam sterilization, for example, reaching the sterilization temperature does not necessarily imply the presence of saturated steam in (direct or indirect) contact with the micro-organisms to be inactivated, this being an indispensable condition for the destruction of the microbic content.

The second monitoring method mentioned above is based on the use of so-called biological indicators or "bioindicators"; these are preparations of special sporogenous (non pathogenic) micro-organisms which are particularly resistant to sterilization. Based on the assumption that the bioindicators are prepared so as to be more resistant to the action of the sterilizing agent—which may be, for example, steam or hot air in the thermal processes or ethylene oxide or hydrogen peroxide in the "cold" chemical processes—than the micro-organisms potentially present in the product to be sterilized, if, at the end of treatment, the destruction of the bioindicators is obtained, then the product may be reasonably regarded as sterilized.

The bioindicators are typically produced by specialized companies in various forms, for example in the form of aqueous suspensions contained in small bottles or phials or else as depositions on porous substrates (made of textiles, paper, elastomers or other material) which are then dried.

The bioindicators are defined by specific parameters; the type of spores used, the number $N_0$ of spores contained in the bioindicator, the speed D of destruction of these spores in relation to the sterilization temperature, the variation z in the aforementioned speed depending on the variation in the sterilization temperature.

The knowledge of and therefore the determination of these parameters is of fundamental importance for being able to use the bioindicator.

However, while the determination of $N_0$ is within the competence of any microbiologist, the determination of D and z is anything but easy and require methods which are laborious and produce non-repetitive results.

This type of treatment is shown graphically in the accompanying FIG. 1.

At the end the bioindicator samples are analyzed in order to count how many spores have survived and then the values of D and z are calculated.

The methods with which this process is performed depend on the way in which the bioindicators are prepared; for example, if they are in the form of an aqueous suspension, one possible method consists in introducing them into thin glass capillary tubes which are closed at at least one end. Said capillary tubes are then treated with special sterilizers able to reach the sterilization temperature (or more generally, the sterilization conditions) in a few seconds and, equally rapidly, able to cool the charge.

The abovementioned apparatuses, known as BIERs (Biological Indicator Evaluator Resistometers) are complex, delicate and very costly, in addition to not being widely available on the market.

Essentially, BIER apparatuses have been developed with the sole aim of allowing measurement of the reduction in the microbic content under sterilization conditions, depending on the variation in the duration of exposure and not during the transient stages (pre- and post-conditioning stages during which a gradual reduction also occurs).

Secondly, for the user it is an extra apparatus to be installed, maintained and overhauled periodically in addition to those which are normally used.

The present invention aims to remedy this state of the art.

The object of the invention, therefore, is to provide a method and the associated apparatus for characterizing bioindicators, which can also be applied to a sterilizer during production.

This object is achieved with a method, the steps for implementation of which are described in the claims which follow.

The invention includes moreover a device for implementing the aforementioned method, the characteristic features of which are also described in the claims; in particular, according to a preferred embodiment of the invention, the apparatus on which the device is installed is a steam sterilizer.

In order to understand the invention more fully it is necessary to consider that, apart from the high speed of the pre-treatment and post-treatment stages, the BIER apparatuses during the actual sterilization step function in exactly the same manner as any other sterilizer, attempting to maintain the maximum uniformity of temperature possible over time and in space for a duration which can be selected by the operator.

The invention therefore aims to allow the bioindicator samples to complete the pre-treatment and post-treatment stages in the shortest time possible within a normal sterilizer, on the assumption that, by introducing the samples into the chamber (already during sterilization), the duration of the transient stages is, at the most, that required for penetration of the heat into the sample and, as such, is totally independent of the characteristics of the apparatus.

Further characteristic features and advantages of the invention will emerge more clearly from the description, provided below by way of a non-limiting illustration, of a preferred and non-exclusive example of embodiment thereof shown in the accompanying drawings.

BRIEF DESCRIPTION OF THE DRAWINGS

FIG. 2 is a perspective view of a sterilizer according to the invention in which the open sterilization chamber allows the guide duct for the bioindicators to be seen;

FIG. 3 shows a front view of the inside of the sterilizer according to FIG. 1 in which the open sterilization chamber allows the guide duct for the bioindicators to be seen;

FIG. 7 shows schematically a variant of the sterilizer according to the invention.

DETAILED DESCRIPTION

Figure 1:
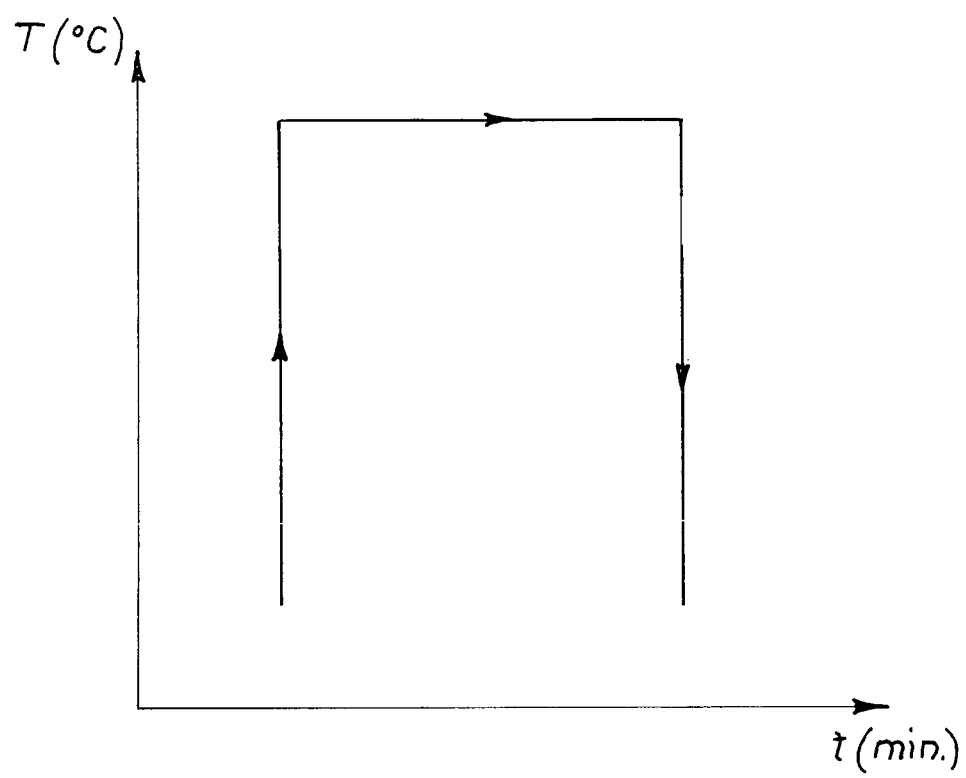
FIG. 1 is a process diagram which shows a heat cycle applied to the biological indicators for the monitoring of "hot" sterilization processes.

In the figures, 1 denotes overall a sterilizer in accordance with the invention, which comprises a sterilization chamber 2 inside which the objects to be treated are deposited.

During use, the chamber 2 is sealed hermetically by a hatch 3 and the steam is supplied inside it in a known manner: for this purpose, in this case, the body 4 of the sterilizer, i.e. its part comprising the wall which encloses the chamber 2 and incorporates the various means for forming and/or supplying the steam, is constructed in a manner known per se, as for example in the sterilizers produced and marketed by the applicants of the present application.

As can be seen, the sterilization chamber 2 is of the horizontal-axis type and is passed through vertically by a duct 5 consisting of a tube screwed at the bottom onto a threaded union 6 on the bottom of the chamber; at the top the duct 5 passes through the wall of the sterilizer and at its end sealingly engages, in a manner known per se (not shown in the drawings), with two ball valves 8 and 9 arranged in series and separated by a prechamber 7. The latter has been designed so as to allow the introduction of bioindicator samples into the sterilization chamber 2 (which contains the sterilizing agent and therefore cannot be placed into direct communication with the exterior) in a manner which is safe for the operator and the process.

The opening (and consequent closing) of the valve 9 allows the introduction of the bioindicator sample into the upper prechamber 7; while the opening (and consequent closing) of the valve 8 causes the sample to fall by means of gravity into the sterilization chamber 2 inside the duct 5.

At the bottom also the duct 5 passes through the wall of the sterilizer and its bottom end is connected to two ball valves 10 and 11 arranged in series and also separated by a prechamber 7; a basin 12, full of balanced water and ice, is situated underneath these valves, for rapid cooling of the bioindicator samples discharged from the chamber at the end of the treatment.

Openings 13 are present in the section of the duct 5 which is situated inside the chamber 2 and which allow free circulation inside it of the sterilizing agent, so as not to alter the conditions with respect to the chamber 2.

The bioindicator samples are contained inside a test tube 15 (denoted by broken lines in FIG. 2 and shown in detail in FIG. 4) which is preferably metallic and two sealed plugs 16 and 17 are screwed onto its ends.

In accordance with a preferred embodiment of the test tube, the plug 16 has a central opening 18 for insertion of the shank 19 of a memory temperature sensor 20; the latter is a device—known per se—in which a thermistor arranged inside the shank 19 transmits the temperature values detected inside the test tube to an electronic circuit which memorizes them.

The test tube 15 has the function of containing the bioindicators in liquid form and with this solution it is possible to adjust precisely the real conditions of the bioindicator, a condition which is impossible to obtain with the conventional sensors connected to the process controller by means of copper conductors.

The test tube 15 thus prepared is introduced from above into the upper prechamber via the valves 8 and 9.

Figure 5:
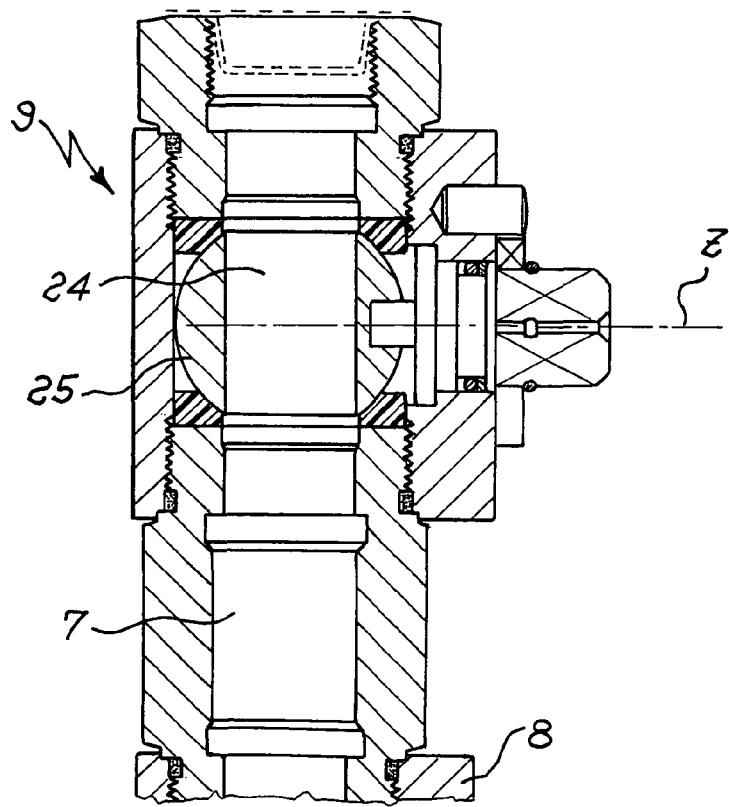
FIG. 5 shows a ball valve present in the abovementioned sterilizer.

FIG. 5 shows the first of these valves in the open condition (the other one is identical and therefore the comments made below will also apply to it), namely with the channel 24 inside the ball 25 aligned vertically with the axis of the duct 5; the closed condition of the same valve occurs instead when, following the rotation through 90° of the ball about the axis Z, the channel 24 assumes a horizontal condition with reference to FIG. 5 (and perpendicular to the sheet of the said figure).

Figure 4:
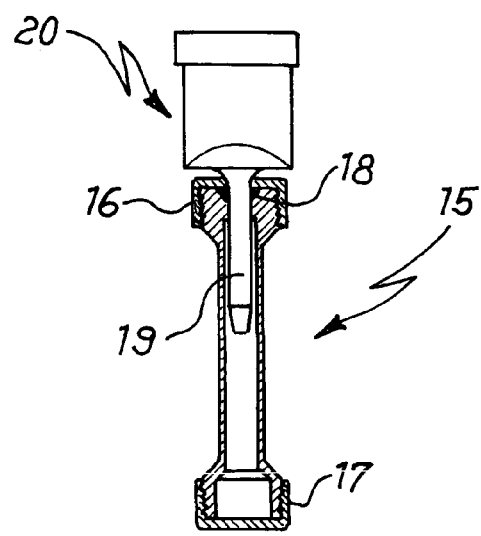
FIG. 4 is a test tube for samples of biological indicators, used in the abovementioned sterilizer, inside which a memory sensor has been inserted.

As can be seen FIGS. 4 and 5 shown intentionally on the same page, when the valve 9 is in the open condition the test tube 15 may be introduced from above into the upper prechamber until it reaches the valve 8 which is situated in the closed condition, such that steam does not escape from the chamber 2; the valve 9 is then closed and the valve 8 opened such that the test tube 15 falls into the duct 5 inside the sterilizer.

The steam present inside the chamber 2 also fills the duct 5 owing to the openings 13 and therefore the test tube 15 which is inside it assumes the sterilization temperature already reached by the chamber of the sterilizer 1.

Recovery of the test tube is performed from underneath the duct 5, operating the two valves 10 and 11 in a similar way to that seen for the valves 8 and 9, namely opening one of them while the other one is kept closed and vice versa, so as to reduce to a minimum the loss of pressure inside the chamber 2.

The test tube thus extracted passes through the bottom prechamber and falls into the basin 12 and the bioindicator sample present inside it is rapidly cooled.

From that described hitherto it is possible to understand how the bioindicator treatment method performed with the sterilizer achieves the object predefined initially for the invention.

In fact, when the test tube 15 is introduced into the duct 5 inside the sterilizer, the bioindicator sample contained inside it is exposed immediately to the sterilization conditions present inside the chamber 2; this corresponds to heating (pre-conditioning step) represented by the substantially vertical first section of the diagram in FIG. 1.

Keeping then the test tube 15 inside the duct 5 for a predefined time, depending on the sterilization cycle which is to be performed on the bioindicator sample, the horizontal section (maintenance step) of the aforementioned diagram is obtained; at the end of this step the test tube 15 is extracted from the duct 5 and falls into the basin 12 where it undergoes sudden cooling, thus obtaining the final vertical section (post-conditioning step) in the diagram of FIG. 1.

The sample present inside the test tube 15 is then fully recovered by unscrewing one or both the sealing plugs 16 or 17.

As can be seen, there are no difficulties associated with the handling of the bioindicator sample since the sole operations to be performed are the opening and closing of the valves 8-11 in order to introduce and extract the test tube 15 from the sterilization chamber.

Moreover, the treatment method according to the invention may be implemented practically with all the various forms of bioindicators available.

It must be emphasized, however, that instead of the metal test tube 15, it is possible to use phials made of glass, plastic or other suitable material able to withstand the thermal and mechanical stresses (such as those caused by falling inside the duct 5) described above and compatible with the type of bioindicator.

All these results are achieved with a machine which is able to perform also the sterilization in production conditions and which in the example is a steam sterilizer (but could also be an ethylene oxide, ozone or hydrogen peroxide sterilizer, an oven or other apparatus), without the need for dedicated and costly machines such as BIERs: it is therefore clear how the invention contributes to remedying the general state of the art described above.

In other words, with the method according to the invention, the bioindicators are subjected to treatment ("hot" or "cold" depending on the type) inside the said chamber where the charge to be sterilized is contained when the sterilizer is used for normal production operations.

This is achieved by simply mounting the device described inside the chamber. It must be noted moreover that this device if necessary could also be kept mounted during any routine sterilization operations performed during production, these not being hampered in fact by the presence of the device even though it constitutes obviously an obstacle for filling of the chamber.

In this connection it must be underlined how this applies not only to the case of steam sterilization, but also to sterilization/dipyrogenation performed in an oven or using other apparatuses equipped with a closed sterilization chamber.

In addition to this, it must be pointed out how the bioindicator treatment according to the invention provides reliable results, since it is obtained in the same conditions as the actual sterilization process, without producing any simulation.

Obviously variants of the invention with respect to that described hitherto may be envisaged.

For example, as regards the means for introducing and extracting the bioindicators inside the sterilizer, various alternatives to the pairs of ball valves 8, 9 and 10, 11 are possible. Therefore, it is possible to have gate valves, or in any case valves which are not ball valves, although they must allow the samples to pass through as described above.

Figure 6:
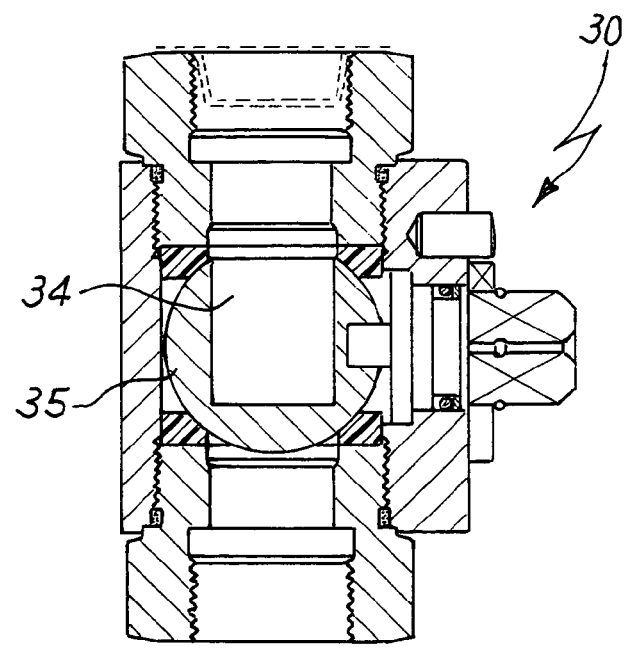
FIG. 6 shows a variant of the ball valve which can be used in the abovementioned sterilizer.

FIG. 6 shows a valve 30 of the ball type, where a seat closed on one side 34 is present instead of the through channel 24 inside the valves 8-10; said seat contains the test tube 15 when it is inserted from above and, in order to allow the test tube to fall inside the duct 5, it is sufficient to rotate the ball 35 through 180° with respect to the condition shown in FIG. 6, directing the open side of the seat 34 downwards.

Since the seat 34 is closed, during rotation of the ball 35, there is not loss of sterilizing agent and therefore with this variant a single valve 34 instead of each of the pair of valves 8, 9 and 10, 11 is sufficient.

Other variants to be taken into consideration are those which can be obtained by automating the operation of the valves; in the example shown the valves are of the manual type, but obviously they may be equipped with electromechanical actuators if necessary associated with the control system of the apparatus or the sterilizer so as to provide an automated system both as regards treatment of the bioindicators and as regards recording of the data for this treatment.

It must also be mentioned that it is possible to provide inside the duct 5 systems for keeping the test tube 15 in a central position relative to its ends, so that, when it is inserted from above, it does not end up at the bottom where the valve 10 is situated.

For this purpose it would be possible to envisage using a spacer consisting of a cylinder made of plastic or other suitable material, to be inserted inside the duct 5 before the test tube 15; in this way the spacer would be positioned on the bottom of the duct in the vicinity of the valve 10, keeping the test tube 15 raised in a more central position with respect to the bottom of the chamber.

The test tube 15 is then extracted from the bottom together with the spacer by operating the valves 10 and 11 as already shown.

As an alternative to the spacer it is possible, however, to envisage also other solutions, for example a diaphragm or any stopping element transversely arranged inside the duct 5 and able to be actuated outside the sterilization chamber 2 (for example by means of a remotely controlled motor).

Finally, it must be pointed out that, although in the example considered, the sterilizer 1 is of the horizontal-axis type and the duct 5 is arranged in the vertical direction so as to favour the introduction and extraction of the test tube by means of gravity, the principles of the invention are also applicable to vertical-axis sterilizers.

An example is a sterilizer with chamber having this arrangement, in which the duct 5 is arranged in a suitable manner so that the test tube is able to pass through the sterilization chamber by means of gravity, or a by-pass which is entirely similar to that described, arranged outside the chamber, but connected to the latter so as to ensure the same conditions present inside the sterilization chamber 2.

This solution with by-pass is shown in FIG. 7, where the same numbering as in the previous example has been used.

As can be seen, the duct 5 is situated outside the body 4 of the sterilizer, but communicates with the sterilization chamber 2 inside it, via two pipes 40 and 41; preferably the duct 5 and the pipes 40, 41 are insulated (in FIG. 7 only the duct 5 is shown cross-sectioned so that the thermal insulation is visible) so as to maintain inside the duct 5 the same temperature conditions as those of the sterilization chamber 2.

The introduction and the extraction of the bioindicator samples is performed in the same manner already described above using the valves 8-10 and the prechambers 7, to which reference should be made for the sake of brevity.

The advantage of this solution is that it is suitable for installation in ready existing sterilizers, using unions or other fittings arranged on the body 4 of the sterilizer.

The invention claimed is:
1. A method for using a bioindicator in a sterilization process, comprising the sequential steps of:
providing a sterilization chamber and a duct, wherein the duct has a top end, central section, and bottom end, wherein the central section is in communication with the sterilization chamber so as to allow a sterilizing agent to flow into and from the central section, wherein each the top end and the bottom end are outside the sterilization chamber and include a valve means;

introducing a sterilizing agent into the sterilization chamber and allowing the sterilizing agent to flow into and from the central section of the duct;

introducing a bioindicator into the top end of the duct;

allowing the bioindicator to pass through the duct from the top end to the bottom end, the bioindicator also being exposed to the sterilizing agent in the central section;

removing the bioindicator from the bottom end of the duct; and analyzing the bioindicator.

2. The method of claim 1 wherein the valve means comprises an inner ball valve and an outer ball valve.

3. The method of claim 1 wherein the valve means comprises an inner valve and an outer valve arranged in series and separated by a prechamber.

4. The method of claim 3 wherein the introducing the bioindicator into the top end of the duct comprises the sequential steps of:
   a. opening the outer valve to introduce the bioindicator into the top end of the duct and to allow the bioindicator to move into the prechamber;
   c. closing the outer valve; and
   c. opening the inner valve to allow the bioindicator to move into the central section.

5. The method of claim 3 wherein the removing the bioindicator from the bottom end of the duct comprises the sequential steps of:
   a. opening the inner valve to allow the bioindicator to move from the central section into the prechamber;
   b. closing the inner valve; and
   c. opening the outer valve to remove the bioindicator from the bottom end of the duct.

6. The method of claim 1 wherein the central section of the duct is arranged inside of the sterilization chamber, the central section having at least one opening that allows for the sterilizing agent in the sterilization chamber to flow into and from the central section of the duct.

7. The method of claim 1 wherein the duct is arranged outside of the sterilization chamber and has a bypass connection that allows for sterilizing agent in the sterilization chamber to flow into and from the central section of the duct.

8. The method of claim 1 wherein the duct is substantially vertical to allow the bioindicator to pass through the duct from the top end to the bottom end by means of gravity.

9. The method of claim 1 wherein the sterilizing agent comprises one or more of the following: water vapor, superheated water, ethylene oxide, hot air, hydrogen peroxide or ozone.

10. The method of claim 1 further comprising placing the bioindicator into a cooling basin after removing the bioindicator from the bottom end of the duct.

11. The method of claim 1 wherein the sterilization chamber is part of a steam or ethylene oxide sterilizer, an oven for hot-air sterilization/depyrogenation, or a machine for treatment with a sterilizing agent.

12. The method of claim 1 wherein the bioindicator comprises spores and the analyzing the bioindicator comprises counting how many spores survived after being exposed to the sterilizing agent.

13. An apparatus for carrying out the method of claim 1, comprising:
   a sterilization chamber; and
   a duct having a top end, central section, and bottom end, wherein the central section is in communication with the sterilization chamber so as to allow a sterilizing agent to flow into and from the central section, wherein each the top end and the bottom end are outside the sterilization chamber and include a valve means.

14. The apparatus of claim 13 wherein the valve means comprises an inner ball valve and an outer ball valve.

15. The apparatus of claim 13 wherein the valve means comprises an inner valve and an outer valve arranged in series and separated by a prechamber.

16. The apparatus of claim 13 wherein the central section of the duct is arranged inside of the sterilization chamber, the central section having at least one opening that allows for the sterilizing agent in the sterilization chamber to flow into and from the duct.

17. The apparatus of claim 13 wherein the duct is arranged outside of the sterilization chamber and has a bypass connection that allows for the sterilizing agent in the sterilization chamber to flow into and from the central section of the duct.

18. The apparatus of claim 13 further comprising a basin that receives the bioindicator after removing the bioindicator from the bottom end of the duct, the basin used to cool or post-condition the bioindicator.

19. The apparatus of claim 13 wherein the sterilization chamber is part of a steam or ethylene oxide sterilizer, an oven for hot-air sterilization/depyrogenation, or a machine for treatment with a sterilizing agent.

20. A method for using a bioindicator in a sterilization process, comprising:
   providing a sterilization chamber and a duct, wherein the duct has a top end, central section, and bottom end, wherein the central section is in communication with the sterilization chamber so as to allow a sterilizing agent to flow into and from the central section, wherein each the top end and the bottom end are outside the sterilization chamber and include a valve means, wherein the valve means comprises an inner valve and an outer valve arranged in series and separated by a prechamber;
   introducing a sterilizing agent into the sterilization chamber and allowing the sterilizing agent to flow into and from the central section of the duct;
   introducing a bioindicator into the top end of the duct using the sequential steps of (a) opening the outer valve to introduce the bioindicator into the top end of the duct and to allow the bioindicator to move into the prechamber, (b) closing the outer valve, and (c) opening the inner valve to allow the bioindicator to move into the central section;
   allowing the bioindicator to be exposed to the sterilizing agent in the central section;
   removing the bioindicator from the bottom end of the duct using the sequential steps of (a) opening the inner valve to allow the bioindicator to move from the central section into the prechamber, (b) closing the inner valve, and (c) opening the outer valve to remove the bioindicator from the bottom end of the duct; and
   analyzing the bioindicator.

* * * * *